(12) United States Patent
Lee et al.

(10) Patent No.: US 6,699,295 B2
(45) Date of Patent: Mar. 2, 2004

(54) MULTI-AXIS PROSTHETIC ANKLE JOINT

(75) Inventors: Chi L. Lee, Columbus, OH (US); James M. Colvin, Hilliard, OH (US); Robert E. Arbogast, Mt. Sterling, OH (US)

(73) Assignee: Ohio Willow Wood Company, Mount Sterling, OH (US)

( * ) Notice: Subject to any disclaimer, the term of this patent is extended or adjusted under 35 U.S.C. 154(b) by 0 days.

(21) Appl. No.: 09/893,887

(22) Filed: Jun. 29, 2001

(65) Prior Publication Data

US 2003/0004582 A1 Jan. 2, 2003

(51) Int. Cl.[7] .................................................. A61F 2/66
(52) U.S. Cl. ........................................... 623/49; 623/52
(58) Field of Search ............................... 623/47–50, 53, 623/52, 54–55

(56) References Cited

U.S. PATENT DOCUMENTS

| | | | | |
|---|---|---|---|---|
| 1,001,641 A | * | 8/1911 | Harrison | 623/47 |
| 1,090,327 A | * | 3/1914 | Milligan | 623/47 |
| 1,400,042 A | * | 12/1921 | Erb | 623/47 |
| 2,066,599 A | * | 1/1937 | Willett | 623/47 |
| 2,215,525 A | * | 9/1940 | Jeter | 623/47 |
| 2,390,920 A | * | 12/1945 | Caron | 623/47 |
| 2,620,485 A | * | 12/1952 | Greissinger | 623/47 |
| 2,692,990 A | * | 11/1954 | Schaefer | 623/47 |
| 2,731,645 A | * | 1/1956 | Woodall | 623/50 |
| 3,956,775 A | * | 5/1976 | Moore | 623/47 |
| 3,982,280 A | | 9/1976 | Asbelle et al. | |
| 4,446,580 A | * | 5/1984 | Furuya et al. | 623/50 |
| 4,461,045 A | | 7/1984 | Shorter et al. | |
| 4,463,459 A | | 8/1984 | Shorter et al. | |
| 4,645,508 A | | 2/1987 | Shorter et al. | |
| 4,792,340 A | | 12/1988 | Aulie et al. | |
| 5,019,109 A | | 5/1991 | Voisin | |
| 5,112,356 A | | 5/1992 | Harris et al. | |
| 5,116,383 A | | 5/1992 | Shorter et al. | |
| 5,376,139 A | | 12/1994 | Pitkin | |
| 5,458,656 A | * | 10/1995 | Phillips | 623/47 |
| 5,766,264 A | | 6/1998 | Lundt | |
| 5,800,563 A | * | 9/1998 | Arbogast et al. | 623/35 |
| 5,800,568 A | | 9/1998 | Atkinson et al. | |
| 5,899,944 A | * | 5/1999 | Phillips | 623/55 |
| 5,957,981 A | * | 9/1999 | Gramnas | 623/47 |
| 5,993,488 A | * | 11/1999 | Phillips | 623/55 |
| 6,120,547 A | * | 9/2000 | Christensen | 623/52 |
| 6,290,730 B1 | * | 9/2001 | Pitkin et al. | 623/49 |

FOREIGN PATENT DOCUMENTS

GB 403 337 12/1933

* cited by examiner

Primary Examiner—Corrine McDermott
Assistant Examiner—Alvin Stewart
(74) Attorney, Agent, or Firm—Oblon, Spivak, McClelland, Maier & Neustadt, P.C.

(57) ABSTRACT

A multi-axis prosthetic ankle includes a bottom component connected to a prosthetic foot, a lower leg connection component connected to a prosthetic lower leg, an elastomeric material securely connecting the bottom component with the lower leg connection component, and a mechanical device suspended in the elastomeric material. The mechanical device is formed of a first bracket connected to the bottom component and a second bracket connected to the lower leg connection component. The first and second brackets interlockingly float in the elastomeric material, and are not in direct contact with one another, thereby permitting relative movement of the bottom component and the lower leg connection component by deformation of the elastomeric material. At least one mechanical stop is positioned to prevent the relative angular movement of the ankle from deforming the elastomeric material beyond the elastic limit thereof.

24 Claims, 4 Drawing Sheets

MULTI-AXIS PROSTHETIC ANKLE JOINT

BACKGROUND OF THE INVENTION

1. Field of the Invention

The present invention relates generally to prosthetic devices, and more particularly to a multi-axis prosthetic ankle joint.

2. Discussion of the Background

A prosthetic ankle is a component which connects a prosthetic foot with a prosthetic lower leg. For smooth walking, especially, across uneven ground, it is important for the ankle to be designed for a full range of foot motion with respect to the lower leg prosthesis. Most prosthetic ankles currently on the market are modular in design and do not provide optimally controlled multi-axis motion. Often the prosthetic ankle has such a low stiffness that it effectively reduces any functional capabilities of the attached prosthetic foot, resulting in a choppy, unnatural and uncomfortable gait. Some ankles require adjustments to the assembly in order to achieve the desired function.

A full range of motion may be accomplished by the use of multiple axes of rotation in the ankle joint. However, conventional prosthetic ankle joints that provide multi-axis motion tend to require extensive maintenance including the replacement of parts in order to function properly. This is because the conventional ankle joint designs require elastic members to slide in contact with either a rigid surface, which is typically metallic, or another elastic surface. This surface-to-surface sliding motion is the primary cause of material breakdown.

SUMMARY OF THE INVENTION

It is therefore an object of the present invention to provide a multi-axis prosthetic ankle joint which does not suffer from the shortcomings of the prior art.

According to a feature of the invention as set forth in the claims, a multi-axis prosthetic ankle comprises a bottom component adapted to be connected to a prosthetic foot, a lower leg connection component adapted to be connected to a prosthetic lower leg, an elastomeric material securely connecting the bottom component with the lower leg connection component, and a mechanical device suspended in the elastomeric material. The mechanical device comprises a first rigid element connected to the bottom component but not to the lower leg connection component, and a second rigid element connected to the lower leg connection component but not to the bottom component. The first and second elements interlockingly float in the elastomeric material, and are not in direct contact with one another, so as to permit relative movement of the bottom component and the lower leg connection component by deformation of the elastomeric material.

By "interlockingly float" it is meant that the first and second elements are suspended in the elastomeric material in close relation to one another, but do not contact one another except through the intermediary of the elastomeric material. Since the deformation of the elastic material permits multi-axis relative movement of the bottom component and the lower leg connection component, including translational movement, the ankle joint of the invention can simulate natural ankle motion by providing plantar flexion, dorsi flexion, inversion, eversion, translation and internal/external rotational movement. Such motion is optimally controlled by the multi-axis deformation of the elastic material, without sacrificing the energy return of the prosthetic foot. Further, since the components of the mechanical device are bonded to, and encased by, the elastomeric material, the ankle has the ability to absorb and damp both rotational and linear impacts.

Since there is no surface-to-surface sliding motion within the ankle, the material breakdown which might otherwise occur due to surface-to-surface sliding motion is reduced or eliminated.

As force is applied to the ankle, the ankle moves in rotation and translation with a fluid motion by deforming the rubber medium. According to a further feature of the invention, at least one mechanical stop is positioned to prevent the relative angular movement of the ankle from deforming the elastic material beyond the elastic limit thereof. Since the deformation of the elastomeric material is thus always kept within the elastic limit, any tendency of breakdown in the elastomeric material is further reduced.

According to a further feature of the invention, the mechanical device comprises a generally U-shaped first part connected to the bottom component so as to define a first aperture, and a generally U-shaped second part connected to the lower leg connection component so as to define a second aperture. The first part floatingly extends through the second aperture, and the second part floatingly extends through the first aperture.

According to yet a further feature of the invention, a multi-axis prosthetic ankle comprises a bottom component adapted to be connected to a prosthetic foot, a lower leg connection component adapted to be connected to a prosthetic lower leg, an elastomeric material securely connecting the bottom component with the lower leg connection component, and mechanical means for limiting a deformation of the elastic material.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
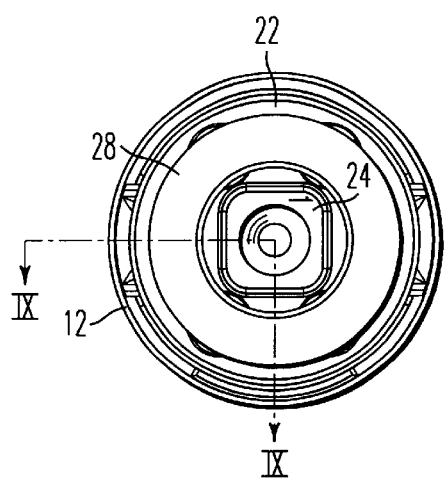
FIG. 1 is a top plan view of an embodiment of a multi-axis prosthetic ankle according to the invention, showing the encasing elastomeric material in phantom lines.
Figure 2:
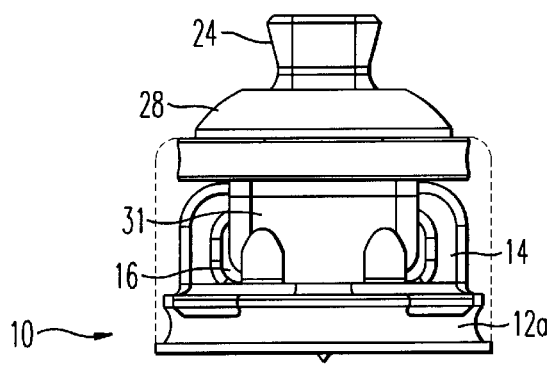
FIG. 2 is a front elevation view of the multi-axis prosthetic ankle of FIG. 1.
Figure 3:
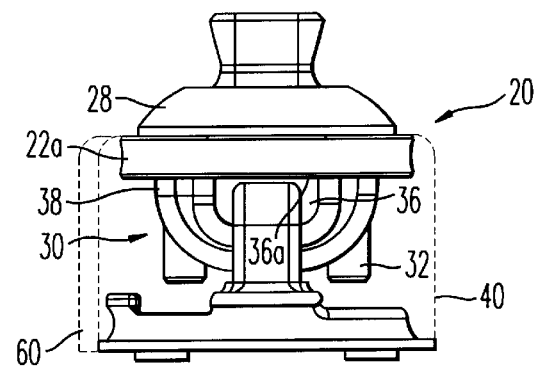
FIG. 3 is a side elevation view of the multi-axis prosthetic ankle of FIG. 1.
Figure 4:
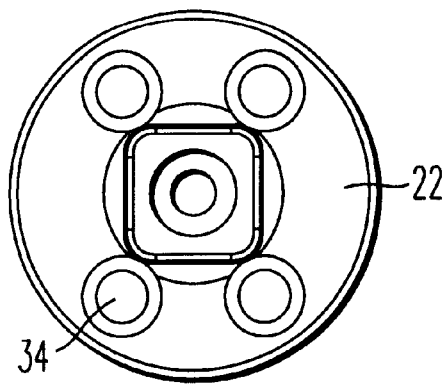
FIG. 4 is a top plan view of the lower leg connection component of the embodiment of FIG. 1.
Figure 5:
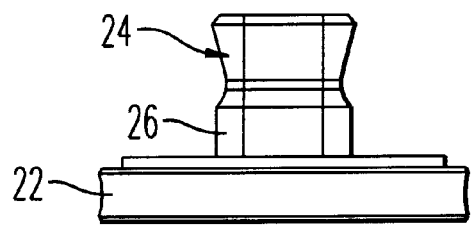
FIG. 5 is a front elevation view of the lower leg connection component of FIG. 4.
Figure 6:
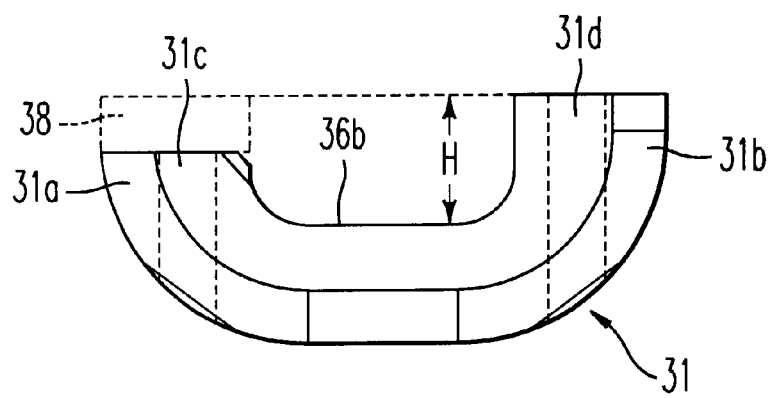
FIG. 6 is a front elevation view of the bracket mounted to the lower leg connection component in FIG. 1.

Referring now to the attached figures which illustrate a non-limiting embodiment of a multi-axis prosthetic ankle according to the invention, and more particularly to FIGS. 1 through 3 which, for clarity of illustration, show the elastomeric casing in phantom lines to reveal the encased components of the mechanical device (rigid mechanical means), the main components of the multi-axis prosthetic ankle are the bottom component 10, the lower leg connection component 20, the mechanical device 30 (rigid mechanical means) and the elastomeric casing 40 bonded to the bottom component and the lower leg connection component, and floatingly encasing the elements of the mechanical device.

Figure 7:
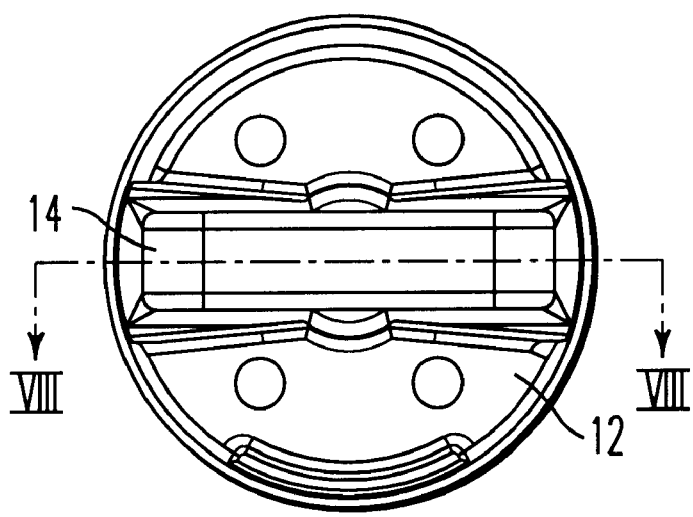
FIG. 7 is a top plan view of the bottom component of the embodiment of FIG. 1.
Figure 8:
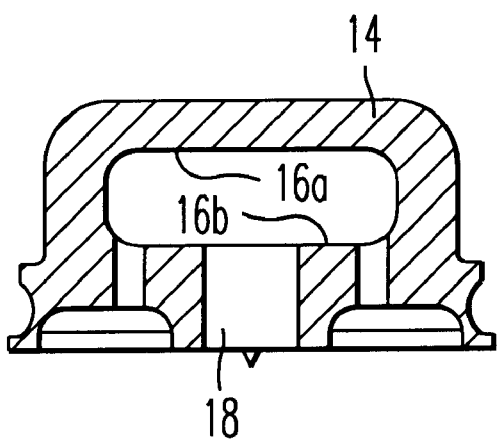
FIG. 8 is a sectional view taken along lines VIII—VIII of FIG. 7.

Referring more particularly to FIGS. 7 and 8, the bottom component 10 comprises a generally circular disk like base 12, and a first "U" shaped bracket 14 (first rigid element) projecting perpendicularly upwardly from the base. The first bracket 14 extends generally diametrically on the base and defines a slot like first aperture 16 having respective top and bottom surfaces 16a and 16b. The base 12 and first bracket 14 are preferably integrally formed from a rigid material such as stainless steel, but could be formed of any other rigid material such as titanium, aluminum or rigid plastic. The base 12 preferably includes a threaded center hole 18 to accept a bolt for the securement of the bottom component 10 to a prosthetic foot.

The lower leg connection component 20 also has a generally circular disk like base 22, and has a pyramid part 24 projecting perpendicularly upward from a central portion of the upper surface of the base 22 for connection of the ankle joint to a lower leg prosthesis. The pyramid part 24 may be of a generally conventional design. The lower leg connection component 20 is also preferably integrally formed of stainless steel, but can also be formed of other rigid materials including titanium, aluminum or rigid plastic. A lower portion 26 of the pyramid part 24 may be circular to accept a separate aluminum snap on dome 28.

A second bracket 31 (second rigid element) is mounted to the lower surface of the base 22, for example by bolts 32 passing through bolt holes 34 in the base 22 and the legs of the second bracket. The second bracket 31 is also "U" shaped to define a slot like second aperture 36 having, when mounted to the base 22, respective top and bottom surfaces 36a and 36b. Moreover, a shim 38 may be positioned between one leg of the bracket 31 and the bottom of the base 22, as will be explained below. To this end, one of the legs 31a of the second bracket 31 is shorter than the other. The bracket 31 is preferably formed of aluminum alloy, but can be formed of other rigid materials, including stainless steel, titanium or a hard plastic.

During assembly of the multi-axis prosthetic ankle, the second bracket 31 is interlockingly positioned within the slot like aperture 16 of the first bracket 14 to form the mechanical device 30, after which the second bracket 31 is bolted to the lower surface of the base 22 of the lower leg connection component 20 via the bolts 32 and the shim 38. At this time, a shim 38 of a proper thickness is selected on the basis described below, and is positioned between the end of the shorter one of the legs of the second bracket 31 and the lower surface of the base 22. As will be readily understood by those skilled in the art, the shim has a through hole for the bolt 32, and the legs 31a and 31b of the second bracket 31 have respective threaded through holes 31c and 31d. The resulting assembly is generally shown in FIGS. 1–3.

Subsequently, the assembly of the bottom component 10, lower leg connection component 20 and the second bracket 31 is placed within a mold (not shown). At this time, the assembly of the lower leg connection component 20 and second bracket 31 is held in a slightly elevated position so that the surfaces 36a and 36b of the second aperture 36 do not contact either of the surfaces 16a or 16b of the first bracket 14. Instead, the second bracket 31 is held so as to float without contact with the first bracket 14. While the ankle components are held in this condition, rubber is injected into the mold and permitted to harden. The rubber is preferably a thermoset rubber polymer having a high resistance and memory under cyclical loading. Examples are butyl rubber, ethylene-propylene rubber, neoprene rubber, nitrile rubber, polybutadiene rubber, polyisoprene rubber, stereo rubber, styrene-butadiene rubber, natural rubber or a combination of two or more of these rubbers.

Figure 9:
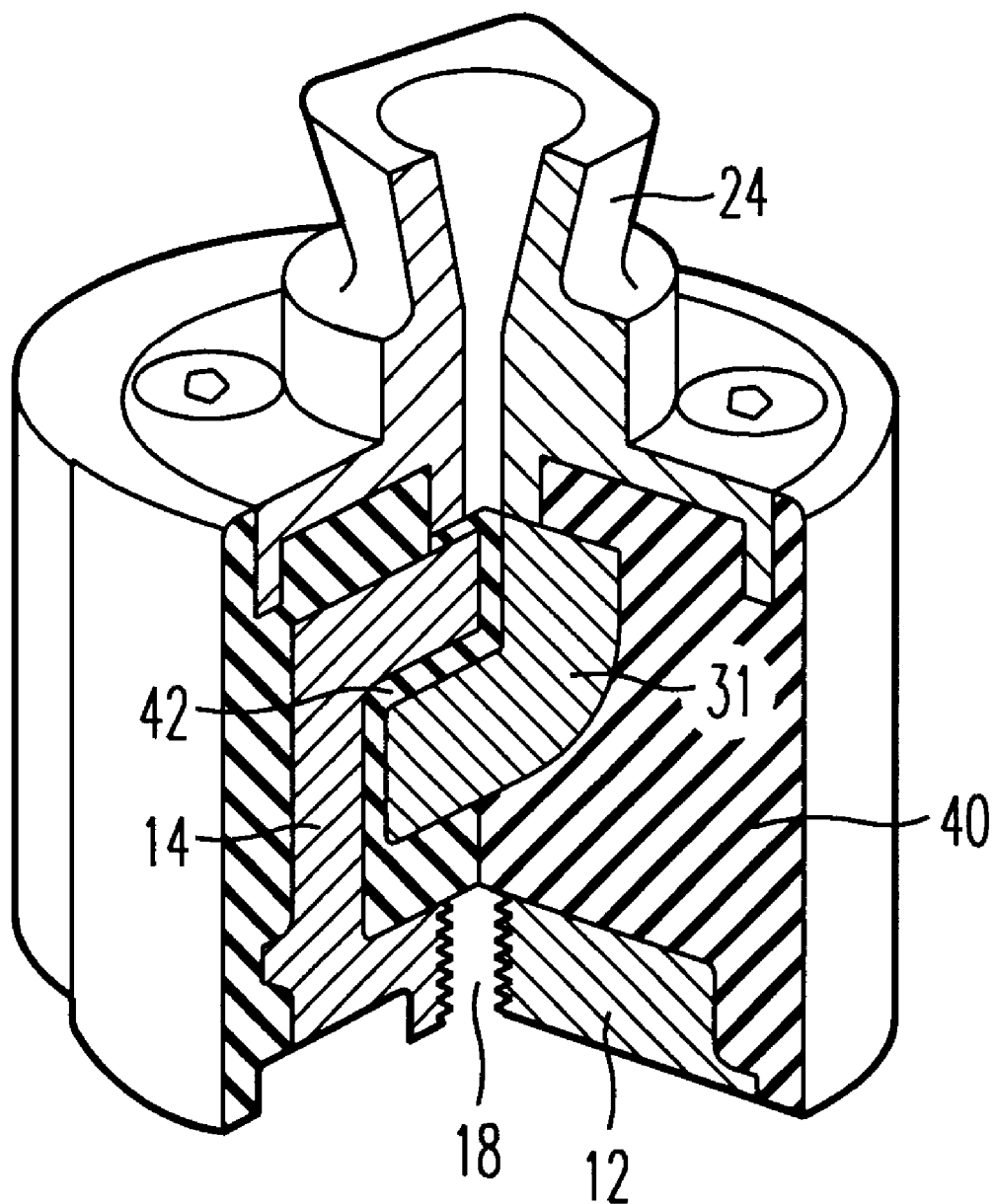
FIG. 9 is a sectional view of taken along lines IX—IX of FIG. 1.

The polymer rubber (elastomeric material) thereby encases and bonds to the bottom component 10, the lower leg connection component 20 and the mechanical device 30 composed of the interlocking brackets 14 and 31. The rigid components are thus fused together with the polymer rubber to form a flexible assembly. This allows for a smooth transition through the entire gait cycle, from heel strike, through midstance to toe off. As can be seen from FIG. 9, the interlocking brackets 14 and 31 do not contact one another but instead are floatingly bonded through the intermediary of the intervening rubber material 42 of the casing 40. The peripheral surfaces of the bases 12 and 22 of the bottom component and the lower leg connection component, respectively, have annular concave recesses 12a and 22a at their circumferential peripheries. These annular recesses improve the grip of the rubber material bonded to the components 10 and 20.

The snap on dome 28 is then mounted to the pyramid part 24, and the ankle assembly is incorporated into a lower leg prosthesis in a conventional manner.

During walking, relative motion (translation and multi-axis rotation) between the bottom component 10 mounted to the foot prosthesis, and the lower leg connection component 20 mounted to the lower leg prosthesis is permitted by the elastic deformation of the rubber material of the casing 40. The motion is thus polycentric and multi-axial with no fixed center of rotation or translation. Moreover, there is no surface to surface contact of the rigid parts 14 and 31 of the mechanical device 30, and so the material breakdown which could otherwise occur due to surface rubbing is minimized or avoided. The rubber material of the casing 40 also absorbs impact energies and so acts as a vibration dampening device.

The casing may optionally include a protruding enlargement 60 at the posterior part of the ankle. The tendon 60 serves to stiffen the ankle when the toe is loaded.

By selecting a shim 38 of the proper thickness, one can control the thickness of the rubber material 42 in the spaces which separate the brackets 14 and 30. One can thereby control the compliance of the joint depending upon the expected loads, which can be anticipated by the weight and general physical activity level of the intended user. This done by selecting a shim 38 providing a desired height "H" for the aperture 36 which allows a predetermined spacing between the brackets, and by the selection of the hardness of the rubber material of the casing 40. A shore hardness A of between 70 and 99 is usually selected for adults, whereas a shore hardness A of between 50 and 70 is usually selected for children. For easy reference, the snap on dome 28 can be color coded to the rubber hardness.

The angular degree of rotational motion between the bottom component 10 and the lower leg connection component 20 is limited by stops. In the preferred embodiment, the stops take the form of a limit of the compression of the rubber material of the casing due to the turning of the interlocking brackets 14 and 31. That is, by selecting a proper shim for providing a desired height "H" for the aperture 36, one also selects the resulting thickness of the rubber material present between the brackets, e.g., the intervening rubber material at 42. As the ankle pivots during walking, the rigid surfaces of the brackets 14 and 31 approach one another while compressing the intervening rubber material of the casing. The resistance of the rubber material to further compression increases as the ankle pivots. When this resistance equals the turning load on the ankle, the rubber material acts as a fixed stop against further rotation. Since the expected load on the ankle and the compression resistance of the rubber material are known, one skilled in the art can select a shim for a desired height "H" to permit a predetermined rotation stop for the ankle. Of course, other forms of the rigid stops could instead be used.

The ankle according to the invention has a higher load range of increasing moment of resistance, compared to prior art ankles which flatten out over lower load ranges. Preferable angles of movement permitted by the stops are as follows:

Internal/External rotation: ±11° to 15°.
Plantar flexion: 13° to 15°.
Dorsi flexion: 13° to 15°.
Inversion/Eversion: ±5° to 10°.
Anterior/Posterior translation: ±0.10 to 0.375 inches.
Medial/Lateral translation: ±0.05 to 0.250 inches.
Vertical displacement: 0.030 to 0.375 inches.

Obviously, numerous modifications and variations of the present invention are possible in light of the above teachings. It is therefore to be understood that the invention may be practiced otherwise than as specifically described herein.

What is claimed is:

1. A multi-axis prosthetic ankle comprising:
   a bottom component adapted to be connected to a prosthetic foot;
   a lower leg connection component adapted to be connected to a prosthetic lower leg;
   an elastomeric material securely connecting said bottom component with said lower leg connection component; and
   a mechanical device suspended in said elastomeric material, said mechanical device comprising a first rigid element connected to said bottom component and not to said lower leg connection component, and a second rigid element connected to said lower leg connection component and not to said bottom component, wherein said first and second elements interlockingly float in said elastomeric material, and are not in direct contact with one another, such as to permit relative movement of said bottom component and said lower leg connection component by deformation of said elastomeric material.

2. The multi-axis prosthetic ankle of claim 1, wherein said elastomeric material is bonded to said bottom component, said lower leg connection component and said mechanical device.

3. The multi-axis prosthetic ankle of claim 1, further comprising at least one mechanical stop adapted to limit rotation of said bottom relative to said lower leg connection component.

4. The multi-axis prosthetic ankle of claim 1, wherein said first rigid element comprises a generally "U" shaped first part connected to said bottom component so as to define a first aperture, and wherein said second rigid element comprises a generally "U" shaped second part connected to said lower leg connection component so as to define a second aperture, wherein said first part floatingly passes through said second aperture and said second part floatingly passes through said first aperture.

5. The multi-axis prosthetic ankle of claim 1, wherein said lower leg connection component includes a pyramid connector and a dome.

6. The multi-axis prosthetic ankle of claim 1, wherein said elastomeric material is a polymer rubber.

7. The multi-axis prosthetic ankle of claim 1, wherein said elastomeric material is a polymer rubber having a shore A hardness of 50 to 99.

8. The multi-axis prosthetic snide of claim 7, further comprising a snap on dome mounted to said lower leg connection component said dome being coded to the hardness of the polymer rubber.

9. The multi-axis prosthetic ankle of claim 1, wherein a height of one of said first and second apertures is adjustable.

10. A multi-axis prosthetic ankle comprising:
    a bottom component adapted to be connected to a prosthetic foot;
    a lower leg connection component adapted to be connected to a prosthetic lower leg;
    an elastomeric material securely connecting said bottom component with said lower leg connection component;
    a generally "U" shaped first rigid part connected to said bottom component so as to define a first aperture;
    a generally "U" shaped second rigid part connected to said lower leg connection component so as to define a second aperture, wherein said first part floatingly extends through said second aperture and said second part floatingly extends through said first aperture.

11. The multi-axis prosthetic ankle of claim 10, wherein said elastomeric material is bonded to said bottom component, said lower leg connection component, and said first and second rigid parts.

12. The multi-axis prosthetic ankle of claim 10, further comprising at least one mechanical stop positioned to prevent a deformation of said elastomeric material from reaching the elastic limit thereof.

13. The multi-axis prosthetic ankle of claim 10, wherein said lower leg connection component includes a pyramid connector and a dome.

14. The multi-axis prosthetic ankle of claim 10, wherein said elastomeric material is a polymer rubber.

15. The multi-axis prosthetic ankle of claim 10, wherein said elastomeric material is a polymer rubber having a shore A hardness of 50 to 99.

16. The multi-axis prosthetic ankle of claim 15, further comprising a snap on dome mounted to said lower leg connection component, said dome being coded to the hardness of the polymer rubber.

17. A multi-axis prosthetic ankle comprising:
    a bottom component adapted to be connected to a prosthetic foot;
    a lower leg connection component adapted to be connected to a prosthetic lower leg;
    an elastomeric material securely connecting said bottom component with said lower leg connection component; and
    rigid mechanical means molded and suspended in said elastomeric material for limiting a deformation of said elastomeric material.

18. The multi-axis prosthetic ankle of claim 17, wherein said lower leg connection component includes a pyramid connector and a dome.

19. The multi-axis prosthetic ankle of claim 17, wherein said elastomeric material is a polymer rubber.

20. The multi-axis prosthetic ankle of claim 1, wherein said elastomeric material is casing having a enlargement located circumferentially opposite the toe of the prosthetic foot when the bottom component is connected to the prosthetic foot.

21. The multi-axis prosthetic ankle of claim 3, wherein the at least one mechanical stop is comprised by a compression resistance of said elastomeric material.

22. The multi-axis prosthetic ankle of claim 21, wherein the elastomeric material is a polymer rubber having a shore hardness A of between 50 and 99.

23. The multi-axis prosthetic ankle of claim 21, wherein the at least one stop permits Internal/External rotation of ±11E to 15E; Plantar flexion of 13E to 15E; Dorsi flexion of 13E to 15E; Inversion/Eversion of ±5E to 10E; Anterior/Posterior translation of ±0.10 to 0.375 inches; Media/Lateral translation of t 0.05 to 0.250 inches; and Vertical displacement of 0.030 to 0.375 inches.

24. A multi-axis prosthetic ankle comprising:

a bottom component adapted to be connected to a prosthetic foot;

a lower leg connection component adapted to be connected to a prosthetic lower leg;

an elastomeric material securely connecting said bottom component with said lower leg connection component; and rigid mechanical means bonded and suspended in said elastomeric material for limiting a deformation of said elastomeric material.

* * * * *